(12) United States Patent
Lehman et al.

(10) Patent No.: US 6,524,577 B1
(45) Date of Patent: Feb. 25, 2003

(54) STRAIN OF STREPTOMYCES FOR CONTROLLING PLANT DISEASES

(75) Inventors: Lori Jo Lehman, Vacaville, CA (US); Randy Jay McCoy, Davis, CA (US); Cai-yao Yuan, Davis, CA (US); Denise Carol Manker, Davis, CA (US); Jimmy Ensio Orjala, Davis, CA (US); Pamela Gail Marrone, Davis, CA (US)

(73) Assignee: AgraQuest, Inc., Davis, CA (US)

( * ) Notice: Subject to any disclaimer, the term of this patent is extended or adjusted under 35 U.S.C. 154(b) by 0 days.

(21) Appl. No.: 09/671,943

(22) Filed: Sep. 27, 2000

(51) Int. Cl.[7] .................. A01N 25/34; A01N 63/00; A01N 63/02; C12N 1/00; C12N 1/20
(52) U.S. Cl. ............... 424/93.43; 424/404; 424/780; 435/253.4; 435/886; 504/117
(58) Field of Search .................. 424/93.1, 93.43, 424/404, 780; 435/243, 822, 253.4, 886; 562/11; 504/117

(56) References Cited

U.S. PATENT DOCUMENTS

| 4,107,297 A | | 8/1978 | Omura et al. ............... 424/122 |
| 5,095,139 A | * | 3/1992 | Loeffler et al. ............... 562/11 |
| 5,403,584 A | | 4/1995 | Crawford et al. ......... 424/93.43 |
| 5,527,526 A | | 6/1996 | Crawford .................. 424/93.43 |

FOREIGN PATENT DOCUMENTS

| EP | 0 408 811 | 1/1991 |
| JP | 63297398 | 5/1988 |
| WO | WO 96/29874 | 10/1996 |
| WO | WO 98/35017 | 8/1998 |

OTHER PUBLICATIONS

Akasaki, K., et al., "Monazomycin, A New Antibiotic Produced by a Streptomyces," *The Journal of Antibiotics. Ser. A.*—*XVI*(3):127–131 (1963).

Axelrood, P.E., et al., "Douglas–fir Root–Associated Microorganisms with Inhibitory Activity Towards Fungal Plant Pathogens and Human Bacterial Pathogens," *Can. J. Microbiol.*—*42*69–700 (1996).

Borges, M., et al., "An achaete–scute Homologue Essential for neuroendocrine Differentiation in the Lung," *Nature*—*386*:852–855 (1997).

Campos, G., et al., "Griseocarnin, an Antifungal Antibiotic Isolated from Streptoverticillium Criseocarneum (IA–7527)," *Rev. Inst. Antibiot (Recife)*—*14*:1–2 (1974) Abstract.

Chamberlain, K., et al., "In vitro and in vivo Antagonism of Pathogenic Turfgrass Fungi by *Streptomyces hygroscopicus* Strains YCED9 and WYE53," *Journal of Industrial Microbiology & Biotechnology*—23:641–646 (1999).

Claridge, C.A., et al., "New Mitomycin Analogs Produced by Directed Biosynthesis," *The Journal of Antibiotics*—*XXXIX*(3):437–446 (1986).

Komori, T., et al., "Isolation of the Aromatic Heptaenic Antibiotics Trichomycin A–F by High–Performance Liquid Chromatography," *Journal of Chromatography*—*481*:416–420 (1989).

Lechevalier, M.P., "Actinomycetes in Agriculture and Forestry," *Actinomycetes in Biotechnolgoy*—327–358 (1988).

Mitscher, L.A. and M. P. Kunstmann, "The structure of neutramycin," Experientia vol. 25, pp. 12–3 (1969).

Reddi, G.S., and A.S. Rao, "Antagonism of soil actinomycetes to some soil–borne plant pathogenic fungi," Indian Phytopathol. vol. 24, pp. 649–657 (1971).

Rothrock, C.S., and D. Gottlieb, "Role of antibiosis in antagonism of *Streptomyces hygroscopicus* var. geldanus to *Rhizoctonia solani* in soil," Can. J. Microbiol., vol. 30, pp. 1440–1447, (1984).

Schwinn et al., "Advances In Plant Pathology: *Phytophthora infestans*, The Cause Of Late Blight Of Potato," (Academic Press, San Diego, p. 244 (1991).

Yuan, W.M., et al., "Characterization of *Streptomyces lydicus* WYEC108 as a Potential Biocontrol Agent Against Fungal Root and Seed Rots," *Applied and Environmental Microbiology*—*61*(8):3119–3138 (1995).

* cited by examiner

Primary Examiner—Francisco Prats
Assistant Examiner—Deborah K. Ware
(74) Attorney, Agent, or Firm—Bingham McCutchen LLP; Antoinette F. Konski (57) ABSTRACT

A novel antibiotic-producing Streptomyces sp. is provided that exhibits antifungal activity only on certain specific plant pathogens. Also provided is a method of treating or protecting plants from fungal infections comprising applying an effective amount of an antibiotic-producing Streptomyces sp. having all the identifying characteristics of NRRL Accession number B-30145. The invention also relates to fungicidal compositions comprising this novel Streptomyces strain and the antibiotics and metabolites produced by this strain either alone, or in combination with other chemical and biological pesticides.

22 Claims, 4 Drawing Sheets

STRAIN OF STREPTOMYCES FOR CONTROLLING PLANT DISEASES

FIELD OF THE INVENTION

The present invention is in the field of biopesticides.

BACKGROUND

For a number of years, it has been known that various microorganisms exhibit biological activity so as to be useful to control plant diseases. Although progress has been made in the field of identifying and developing biological pesticides for controlling various plant diseases of agronomic and horticultural importance, most of the pesticides in use are still synthetic compounds. Many of these chemical fungicides are classified as carcinogens by the EPA and are toxic to wildlife and other non-target species. In addition, pathogens may develop resistance to chemical pesticides (Schwinn et al., 1991).

Biological control offers an attractive alternative to synthetic chemical fungicides. Biopesticides (living organisms and the compounds naturally produced by these organisms) can be safer, more biodegradable, and less expensive to develop.

The actinomycetes, including the streptomycetes, are known producers of antifungal metabolites (Lechavalier and Waksman, 1962; Lechavalier, 1988). Several actinomycete-produced antibiotics are routinely used in an agricultural setting such as streptomycin and terramycin for fire blight control.

Streptomycetes have demonstrated both in vitro and in vivo activity against plant pathogens. Axelrood et al. (1996) isolated 298 actinomycetes from Douglas-fir roots.

Approximately 30% of these strains demonstrated antifungal activity against Fusarium, Cylindrocarpon, and/or Pythium in vitro. Yuan and Crawford (1995) reported that *Streptomyces lydicus* WYEC108 showed both strong in vitro antifungal activity and inhibition of Pythium root rot in pot tests with pea or cotton seed. Reddi and Rao (1971) controlled Pythium damping-off in tomatoes and Fusarium wilt of cotton with *Streptomyces ambofaciens*. Rhizoctonia root rot was controlled by *Streptomyces hygroscopicus* var. *geldanus* (Rothrock and Gottlieb, 1984). These authors reported that the control was dependent on the in situ geldanamycin concentration produced by this strain. The same authors also saw protection of soybeans from *Phytophthora megasperma* var. *sojae* by *Streptomyces herbaricolor* and *Streptomyces coeruleofuscus* (1984). Chamberlain and Crawford (1999) saw in vitro and in vivo antagonism of turfgrass fungal pathogens by *S. hygroscopicus* strain YCED9. Crawford (1996) patented the use of this strain to control plant pathogens in U.S. Pat. No. 5,527,526. Suh (1998) patented 2 Streptomyces sp. that were active against *Rhizoctonia solani* and *Phytophthora capsici*. A *Streptomyces griseoviridis* product against Fusarium spp. and other soil pathogens is on the market as Mycostop™.

DISCLOSURE OF THE INVENTION

A novel antibiotic-producing Streptomyces sp. is provided that exhibits antifungal activity only on certain specific plant pathogens. Also provided is a method of treating or protecting plants from fungal infections comprising applying an effective amount of an antibiotic-producing Streptomyces sp. having all the identifying characteristics of NRRL Accession number B-30145. The invention also relates to fungicidal compositions comprising this novel Streptomyces strain and the antibiotics and metabolites produced by this strain either alone, or in combination with other chemical and biological pesticides.

The antibiotic-producing Streptomyces sp. can be provided as a suspension in a whole broth culture or as an antibiotic-containing supernatant obtained from a whole broth culture of an antibiotic-producing Streptomyces sp. Also provided is a novel butanol-soluble antibiotic that exhibits specific antifungal activity.

MODES FOR CARRYING OUT THE INVENTION

The present invention provides a novel strain of Streptomyces sp. or mutants thereof with antifungal activity only on specific plant pathogens such as Alternaria, Phytophthora, Botrytis, Rhizoctonia and Sclerotinia. This novel strain was deposited with the NRRL on Jul. 20, 1999 under the provisions of the Budapest Treaty on the International Recognition of the Deposit of Microorganisms for the Purpose of Patent Procedure under Accession No. B-30145. The invention also includes methods of preventing and treating fungal diseases in plants using such bacterial strains or antibiotic-containing supernatants or pure antibiotics obtained from such bacterial strains. The invention also includes a butanol soluble antifungal antibiotic with a molecular weight of less than 10,000 daltons, with stability to base and to heat treatment of 1 hour at 80° C. and lability to acid treatment.

Definitions

The singular form "a," "an" and "the" include plural references unless the context clearly dictates otherwise. For example, the term "a cell" includes a plurality of cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

As used herein, "biological control" is defined as control of a pathogen or insect by the use of a second organism.

Known mechanisms of biological control include enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fungi" includes a wide variety of nucleated spore-bearing organisms that are devoid of chlorophyll. Examples of fungi include yeasts, molds, mildews, rusts, and mushrooms.

The term "bacteria" includes any prokaryotic organism that does not have a distinct nucleus.

"Pesticidal" means the ability of a substance to increase mortality or inhibit the growth rate of plant pests.

"Fungicidal" means the ability of a substance to increase imortality or inhibit the growth rate of fungi.

"Antibiotic" includes any substance that is able to kill or inhibit a microorganism. Antibiotics may be produced by a microorganism or by a synthetic process or semisynthetic process. The term, therefore, includes a substance that inhibits or kills fungi for example, cycloheximide or nystatin.

"Antifungal" includes any substance that is able to kill or inhibit the growth of fungi.

The term "culturing" refers to the propagation of organisms on or in media of various kinds. "Whole broth culture" refers to a liquid culture containing both cells and media. "Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment and protection, an "effective amount" is that amount sufficient to ameliorate, stabilize, reverse, slow or delay progression of the fungal or bacterial disease states.

"Positive control" means a compound known to have pesticidal activity. "Positive controls" include, but are not limited to commercially available chemical pesticides. The term "negative control" means a compound known not to have pesticidal activity. Examples of negative controls are water or ethyl acetate.

The term "solvent" includes any liquid that holds another substance in solution. "Solvent extractable" refers to any compound that dissolves in a solvent and which then may be isolated from the solvent. Examples of solvents include, but are not limited to, organic solvents like ethyl acetate.

The term "metabolite" refers to any compound, substance or byproduct of a fermentation of a microorganism that has pesticidal activity. Antibiotic as defined above is a metabolite specifically active against a microorganism.

The term "mutant" refers to a variant of the parental strain as well as methods for obtaining a mutant or variant in which the pesticidal activity is greater than that expressed by the parental strain. The "parent strain" is defined herein as the original Streptomyces strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those practiced in the art.

A "composition" is intended to mean a combination of active agent and another compound, carrier or composition, inert (for example, a detectable agent or label or liquid carrier) or active, such as an adjuvant. Examples of agricultural carriers are provided below.

We describe a novel antibiotic-producing strain of Streptomyces sp. NRRL No. B-30145 and mutants thereof that have antifungal activity only on specific plant pathogens. Also provided is a supernatant isolated from the culture as well as a composition comprising the culture. In a further aspect, the compositions further comprise at least one chemical or biological pesticide.

A metabolite produced by the Streptomyces sp. strain is also provided by this invention. The metabolite exhibits activity against plant pathogenic fungi and is heat and base stable, is acid labile and has a molecular weight of less than 10,000 daltons. The metabolite can also be formulated as a composition, with a carrier or alternatively, with an at least one chemical or biological pesticide.

In order to achieve good dispersion and adhesion of compositions within the present invention, it may be advantageous to formulate the whole broth culture, supernatant and/or metabolite/antibiotic with components that aid dispersion and adhesion. Suitable formulations will be known to those skilled in the art (wettable powders, granules and the like, or can be microencapsulated in a suitable medium and the like, liquids such as aqueous flowables and aqueous suspensions, and emulsifiable concentrates). Other suitable formulations will be known to those skilled in the art.

The strain, culture, supernatant and isolated metabolite are useful to protect or treat plants, fruit, and roots from fungal infections by applying an effective amount of the active formulation to the plant, fruit or root. The formulations are particularly suited to treat or prevent infections caused by a fungus selected from the group consisting of *Alternaria solani, Botrytis cinerea*, Rhizoctonia sp., Sclerotinia sp., and Phytophthora sp.

All patents and publications cited herein are incorporated by reference. Full bibliographic citations for these may be found at the end of the specification, immediately preceding the claims.

The following examples are provided to illustrate the invention. These examples are not to be construed as limiting.

EXAMPLES

Example 1

Characterization of Strain NRRL No. B-30145

NRRL No. B-30145 was identified based on 16S rRNA sequencing. The protocol used to generate the 16S rRNA gene data sequence (Acculab Customer Handbook v. 1.0) is described as follows.

The 16S rRNA gene is PCR amplified from genomic DNA isolated from bacterial colonies. Primers used for the amplification correspond to *E. coli* positions 005 and 531. Amplification products are purified from excess primers and dNTPs using Microcon 100 (Amicon) molecular weight cut-off membranes and checked for quality and quantity by running a portion of the products on an agarose gel.

Cycle sequencing of the 16S rRNA amplification products is carried out using AmpliTaq FS DNA polymerase and dRhodamine dye terminators. Excess dye-labeled terminators were removed from the sequencing reactions using a Sephadex G-50 spin column. The products are collected by centrifugation, dried under vacuum and frozen at −20° C. until ready to load. Samples are re-suspended in a solution of formamide/blue dextran/EDTA and denatured prior to loading. The samples are electrophoresed on an ABI Prism 377 DNA Sequencer. Data are analyzed using PE/Applied Biosystem's DNA editing and assembly software. Once obtained, sequences are compared against PE/Applied Biosystem's MicroSeq™ database using MicroSeq™ sequence analysis software. Sequences are also compared to the GenBank and Ribosomal Database Project (RDP).

The result of the 16S rRNA sequencing identified NRRL No. B-30145 as a Streptomyces sp. This strain may belong to the species *S. mashuensis* (formerly *Streptoverticillium mashuense*) or a related species, as suggested by the sequencing results. The best match was *Streptomyces mashuensis* with a 98% match score.

Example 2

Activity of NRRL No. B-30145 Against Plant Pathogens in in-vitro Culture (Zone Assay)

NRRL No. B-30145 was tested against an array of different plant pathogens utilizing two different in-vitro assays. The agar diffusion (zone) assay consists of applying either plant pathogen spores over the surface of an agar medium to create an entire lawn of growth or utilizing a mycelial agar plug placed in the center of the petri dish that will grow and colonize the agar. Circular wells approximately 7.0 mm in diameter are removed from the agar using a pipette attached to a vacuum pump. Fermentation samples of NRRL No. B-30145 are added to each well along with known standards and water checks. Plates are incubated for three to four days under environmental conditions conducive for each pathogen. Results consist of a zone of no pathogen growth around the well or a greatly reduced amount of pathogen growth around the well or no affect. The size and type of zone is recorded for each sample. Results for NRRL No. B-30145 in agar diffusion assays are presented in Table 1. Results within agar diffusion were variable; diffusion through agar may be inhibited.

TABLE 1

Activity of NRRL No. B-30145 against selected plant pathogens in the agar diffusion (zone) assay.

| Alternaria brassicicola | No Zone/Weak Activity |
|---|---|
| Botrytis cinerea | Weak Activity |
| Monilinia fructicola | No Zone |
| Phytophthora capsici | Moderate activity |
| Pythium sp. | Weak Activity |
| Colletotrichum acutatum | No Zone |
| Rhizoctonia solani | No Zone |
| Sclerotinia sclerotiorum | No Zone |

The second type of in-vitro assay performed to test the pathogen spectrum of NRRL No. B-30145 was the slide germination assay. Fermentation samples of NRRL No. B-30145 at various dilutions were added to glass depression slides (25 mm×75 mm with 18 mm diameter depression 1.75 mm deep) and an equal volume of pathogen spores were mixed with the sample. Slides were incubated on moistened paper towels in sealed plastic boxes at room temperature overnight. Results are determined by observing the fermentation sample/spore suspension sample using a compound microscope at 100×. Typical results consist of lack of germination of the pathogen propagule or greatly reduced germination and/or growth. In addition, various types of malformations of the initial growth from the pathogen spores may occur. The spectrum of activity of NRRL No. B-30145 is presented in Table 2. Complete inhibition of spore germination occurred at low concentrations of fermentation samples.

TABLE 2

Activity of NRRL No. B-30145 against selected plant pathogens in the slide germination assay.

| Alternaria brassicicola | No Germination |
|---|---|
| Alternaria dauci | No Germination |
| Botrytis cinerea | No Germination |
| Monilinia fructicola | No Germination |

Example 3

Activity of NRRL Against Plant Pathogens in Plant Bioassay Tests

Activity of NRRL No. B-30145 was tested against tomato late blight (*Phytophthora infestans*), tomato early blight (*Alternaria solani*), gray mold (*Botrytis cinerea*), turf brown patch (Rhizoctonia sp.), and peanut southern blight (*Sclerotinia minor*). All tests were conducted under controlled environment in the laboratory with plant material grown from seed under typical commercial greenhouse conditions.

Tomato Late Blight—*Phytophthora infestans*

The pathogen is grown on rye agar in standard petri dishes at 16° C. in the dark. Sporangia are collected by flooding the plate with water and scraping the mycelium to dislodge the sporangia. The sporangial suspension is passed through cheesecloth, quantified and adjusted to $1.0 \times 10^4$. Tomato seedlings at the $3^{rd}$ to $5^{th}$ leaf stage are sprayed to run-off with the fermentation sample of NRRL No. B-30145 using an artist airbrush at 40 psi. Treated seedlings are allowed to air dry at room temperature for at least two hours then inoculated with the sporangial suspension by lightly spraying the upper surfaces of the tomato seedlings using a hand held sprayer. Inoculated seedlings are placed in solid bottom flats filled with water and then are covered with a plastic dome to maintain leaf wetness. Flats are incubated at 20° C. with a 14-hr photoperiod for four days continuously covered by the plastic domes. Seedlings are then rated based on a disease rating scale from 0–5 with 0 equaling no symptoms, and 5 equaling 75% or more of the foliage colonized by the pathogen. A typical example of a late blight test is presented in Table 3.

TABLE 3

Results of NRRL No. B-30145 treated tomato seedlings against the late blight pathogen *Phytophthora infestans*.

| Treatment | Ave. D.I. | Replications 1–4 | | | |
|---|---|---|---|---|---|
| Sample 990702 | 1.1 | 1.0 | 0.5 | 2.0 | 1.0 |
| Sample 990709 | 1.1 | 1.0 | 2.0 | 1.0 | 0.5 |
| Sample 990825 | 1.3 | 1.5 | 1.0 | 1.5 | 1.0 |
| Sample 990913 | 1.0 | 1.0 | 1.0 | 1.5 | 0.5 |
| Quadris 30 ppm | 0.1 | 0 | 0.5 | 0 | 0 |
| Water Check | 4.3 | 4.0 | 4.0 | 5.0 | 4.0 |

Samples are different fermentations of NRRL No. B-30145.
D.I. is Disease Index.

Tomato Early Blight—*Alternaria solani*

The pathogen is first grown on commercial Difco potato dextrose agar (PDA) at 22–25° C. under 14-hour lights until the entire plate is covered. The fungus and the agar medium is then cut into small squares approximately 10 mm square and placed fungus side up on a specialized sporulation medium (S-Medium: 20 g sucrose, 20 g calcium carbonate, 20 g Bacto-agar per liter). The S-Media plates are flooded with a thin layer of water and incubated 2–3 days at 22–25° C. under 14-hour lights until full sporulation of the pathogen occurs. Plates are then flooded with water and the agar squares are scraped from the plate. The suspension is passed through cheesecloth and the spores are quantified and adjusted to $1.0 \times 10^5$. Tomato seedlings at the $3^{rd}$ to $5^{th}$ leaf stage are then sprayed until run-off using an artist airbrush as described previously. Treated seedlings are allowed to dry and then inoculated with the spore suspension. Seedlings are placed in flats and covered as described previously and incubated at 25° C. with a 14-hour photoperiod. Seedlings are rated based on a scale of 0–5 as previously described. Results from a typical test are presented in Table 4.

TABLE 4

Activity of NRRL No. B-30145 against the early blight pathogen *Alternaria solani*.

| Treatments | Ave D.I. | Replications | | | |
|---|---|---|---|---|---|
| Test-1 | | | | | |
| Sample 990216 | 1.0 | 2.0 | 0.5 | 0.5 | |
| Quadris 60 ppm | 1.8 | 1.5 | 2.5 | 1.5 | |
| Water Check | 4.0 | 3.0 | 4.0 | 5.0 | |
| Test-2 | | | | | |
| Sample 990216 | 1.1 | 1.5 | 1.0 | 1.0 | 1.0 |
| Water Check | 4.5 | 5.0 | 4.0 | 4.0 | 5.0 |

D.I. is Disease Index.

Pepper Gray Mold—*Botrytis cinerea*

The pathogen is grown on standard PDA under a 14-hour photoperiod at 22° C. until the fungal growth has completely covered the plate (7–9 days). Spores are collected by flooding the plate with water and then gently scraping with a spatula to dislodge the spores. The spore suspension is passed through cheesecloth and quantified and adjusted to $1.5 \times 10^6$. Pepper seedlings are grown until the $4^{th}$ to $6^{th}$ true leaf stage and fermentation samples are sprayed on the upper leaf surfaces using an artist airbrush as described previously. Treated seedlings are inoculated, placed in flats and covered with plastic domes. Flats are placed at 20° C. under continuous darkness for 2.5 days. Seedlings are rated on a 0–5 scale as described previously. Table 5 depicts results from two typical tests.

TABLE 5

Activity of NRRL No. B-30145 against *Botrytis cinerea*

| Treatment | Ave D.I. | Replications | | | |
|---|---|---|---|---|---|
| Test-1 | | | | | |
| Sample 990216 | 1.4 | 1.5 | 1.5 | 1.5 | 1.0 |
| Break 20 ppm | 0.1 | 0 | 0 | 0.5 | 0 |
| Water Check | 4.0 | 4.0 | 4.0 | 3.0 | 5.0 |
| Test-2 | | | | | |
| Sample 990216 | 1.9 | 1.5 | 2.0 | 2.0 | 2.0 |
| Break 20 ppm | 0.8 | 0 | 1.5 | 1.0 | 0.5 |
| Water Check | 4.5 | 4.0 | 5.0 | 5.0 | 4.0 |

D.I. is Disease Index.

Turf Brown Patch—*Rhizoctonia* sp.

Two ml of fermentation sample was added to each cell of a 6-cell pot of one-month old turf seedlings (Bentgrass). A 4 mm mycelial plug of a 2–3 day old culture of Rhizoctonia sp. was placed under the soil surface. Each treatment was replicated 6 times. Inoculted pots were placed in plastic flats and covered with a plastic dome. The flats were placed on a light rack (16 Hr/day) and incubated at room temperature. Disease severity was evaluated after 5–6 days incubation and compared with the water treated control. The results indicated that NRRL No. B-30145 has a suppressive activity against Rhizoctonia (Table 6).

TABLE 6

The efficacy of NRRL No. B-30145 on turf disease caused by *Rhizoctinia* sp.

| Treatment | Dilution Factor | Rep 1 | Rep 2 | Rep 3 | Rep 4 | Rep 5 | Rep 6 |
|---|---|---|---|---|---|---|---|
| 30145 | 1x | +* | + | + | + | + | + |
| 30145 | ½x | + | + | + | + | + | + |
| Water | | +++ | +++ | +++ | +++ | +++ | +++ |

*"+" = light symptoms,
"+++" = severe symptoms

Peanut Southern Blight—*Sclerotinia minor*

Peanut seedlings at the first 2-leaf stage were treated with NRRL No. B-30145 and a 4-mm mycelial plug is placed on the base of each stem after the treated plants dried. Inoculated plants were incubated in a dew chamber for 2 days before being placed in a plastic flat sealed with a cover dome. The flat was incubated on a light rack (16 Hr/day) at room temperature for 10 days. Disease severity was assessed by comparing the treated with the water control. The results (Table 7) indicated NRRL No. B-30145 whole broth at 1× has some controlling activity against *Sclerotinia minor*.

TABLE 7

The efficacy of NRRL No. B-30145 on peanut Sclerotinia blight.

| Treatment | Dilution Factor | Rep 1 | Rep 2 | Rep 3 |
|---|---|---|---|---|
| 30145 | 1x | +/− | 0 | +/− |
| 30145 | ½x | ++ | ++ | + |
| 30145 | ¼x | 0 | ++ | ++ |
| Water | | +++ | +++ | +++ |

*"+/−" indicates strong suppression,
0 indicates no infection,
"+" = light symptoms,
"+++" = severe symptoms,.

Example 5

Antifungal Metabolite Produced by NRRL No. B-30145

The whole broth of NRRL No. B30145 was partitioned into ethyl acetate, butanol and aqueous fractions. Each fraction was tested against *Alternaria brassicicola* in a spore germination assay. The Alternaria spores were germinated in the presence of each sample in a depression microscope slides containing 40 µl of sample and 20 µl of pathogen spores. Approximately 16 hours later the spores are observed under a microscope to see if they have germinated. No germination (score of 0) compared to the water control (100% germination and growth=score of 5) indicates activity of the sample being tested. Results of the Alternaria germination assay with different NRRL No. B-30145 fractions are shown below (score on a 0 to 5 rating as above).

| Fraction | Score | | |
|---|---|---|---|
| | Rep 1 | Rep 2 | Rep 3 |
| Ethyl acetate | 3 | nd | 4 |
| n-butanol | 0 | 0.2 | 1 |
| Aqueous | 0 | 5 | 5 |
| Whole broth | 0 | 0.2 | 0 |
| Water Check | 5 | 5 | 5 |

The metabolite is clearly in the butanol soluble fraction and is not readily extractable in ethyl acetate. Other characteristics of the metabolite were determined. The molecule was shown to pass through a 10,000 molecular weight cut off filter indicating the metabolite is smaller than 10,000 daltons. The activity was not lost when treated with base or upon heating to 80 degrees C. for one hour. The activity was lost when treated with acid (the score against Alternaria increased from 0 to 5).

Fractionation of the butanol extract on octadecylsilane bonded to silica gel (ODS) using an acetonitrile (ACN)/water gradient with 0.01% triflouroacetic acid (TFA) yielded an active fraction eluting with 50% acetonitrile/water with 0.01% TFA. Fractions were tested in an Alternaria germination assay for activity (0–5 rating scale).

| Fraction | Score |
|---|---|
| ODS 10% ACN | 4 |
| ODS 20% ACN | 5 |
| ODS 50% ACN | 0.5 |
| ODS 100% ACN | 5 |
| Water Check | 5 |

Further purification by ODS HPLC yielded 2 active components (Fraction 6 and 7) from an isocratic elution with 31% acetonitrile in water with 0.02% TFA).

| Fraction | Score |
|---|---|
| HPLC Fr. 1 | 5 |
| HPLC Fr. 2 | 5 |
| HPLC Fr. 3–5 | 4 |
| HPLC Fr. 6 | 3 |
| HPLC Fr. 7 | 2 |
| HPLC Fr. 8 | 5 |
| HPLC Fr. 9 | 5 |
| Water Check | 5 |

Figure 1A:
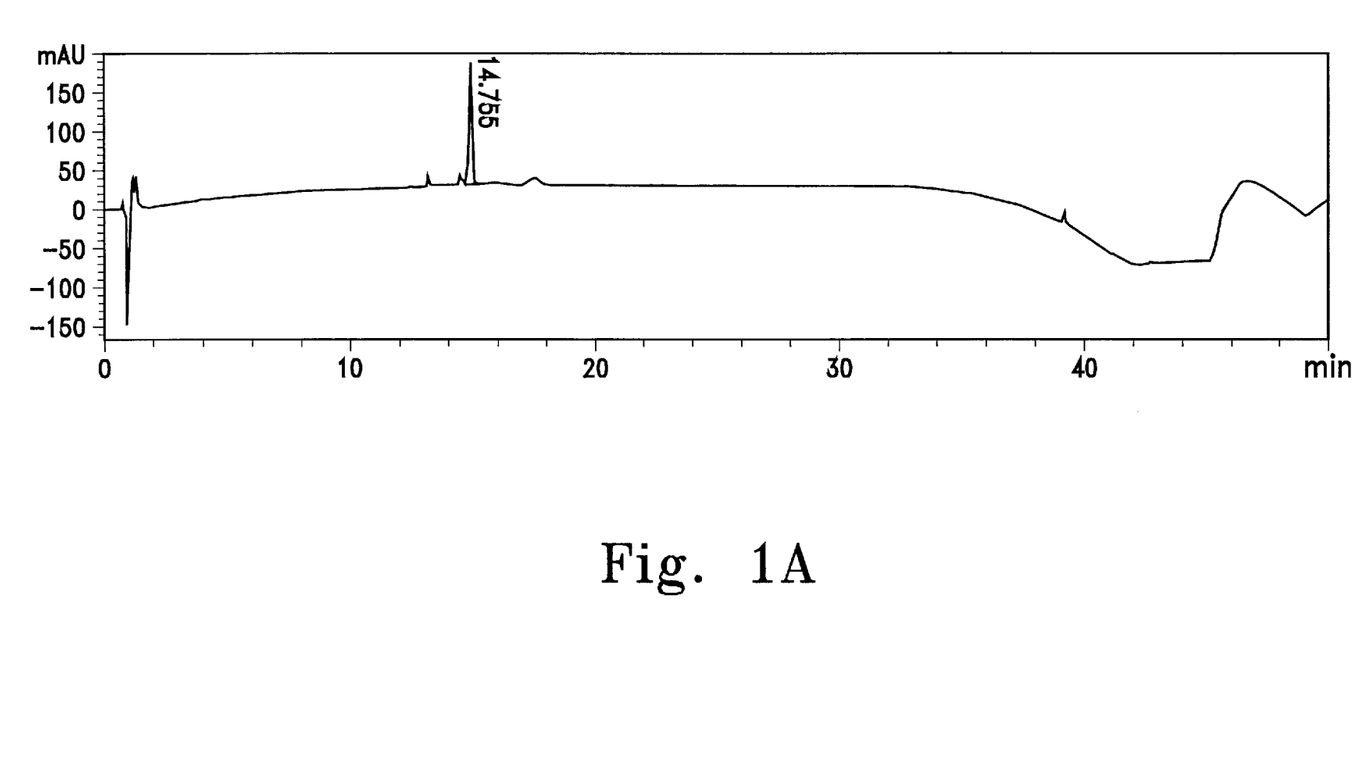
FIG. 1A is the HPLC chromatogram of the active 50% acetonitrile/water with 0.01% TFA fraction 6. DAD1A, Sig=210.4; Ref.=450.80; (E:\J052199\48000003.D). Peak at 14.755.
Figure 1B:
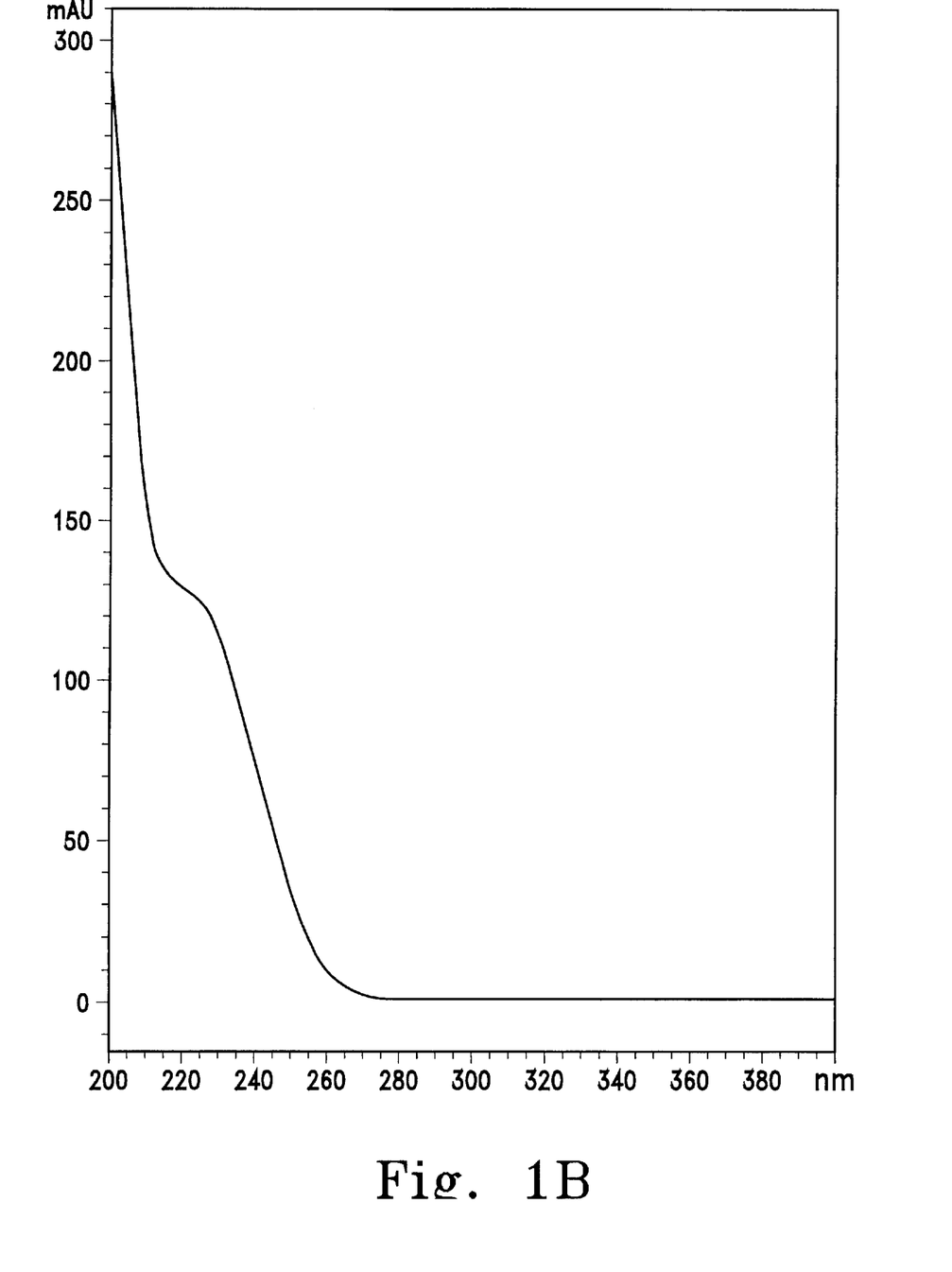
FIG. 1B is the UV Apex spectrum of peak 14.755 (FIG. 1A) of 48000003.D. DAD1; 14.755 (291 mAU, -); Ref.= 14.635 & 14.889 of 48000003.D
Figure 2A:
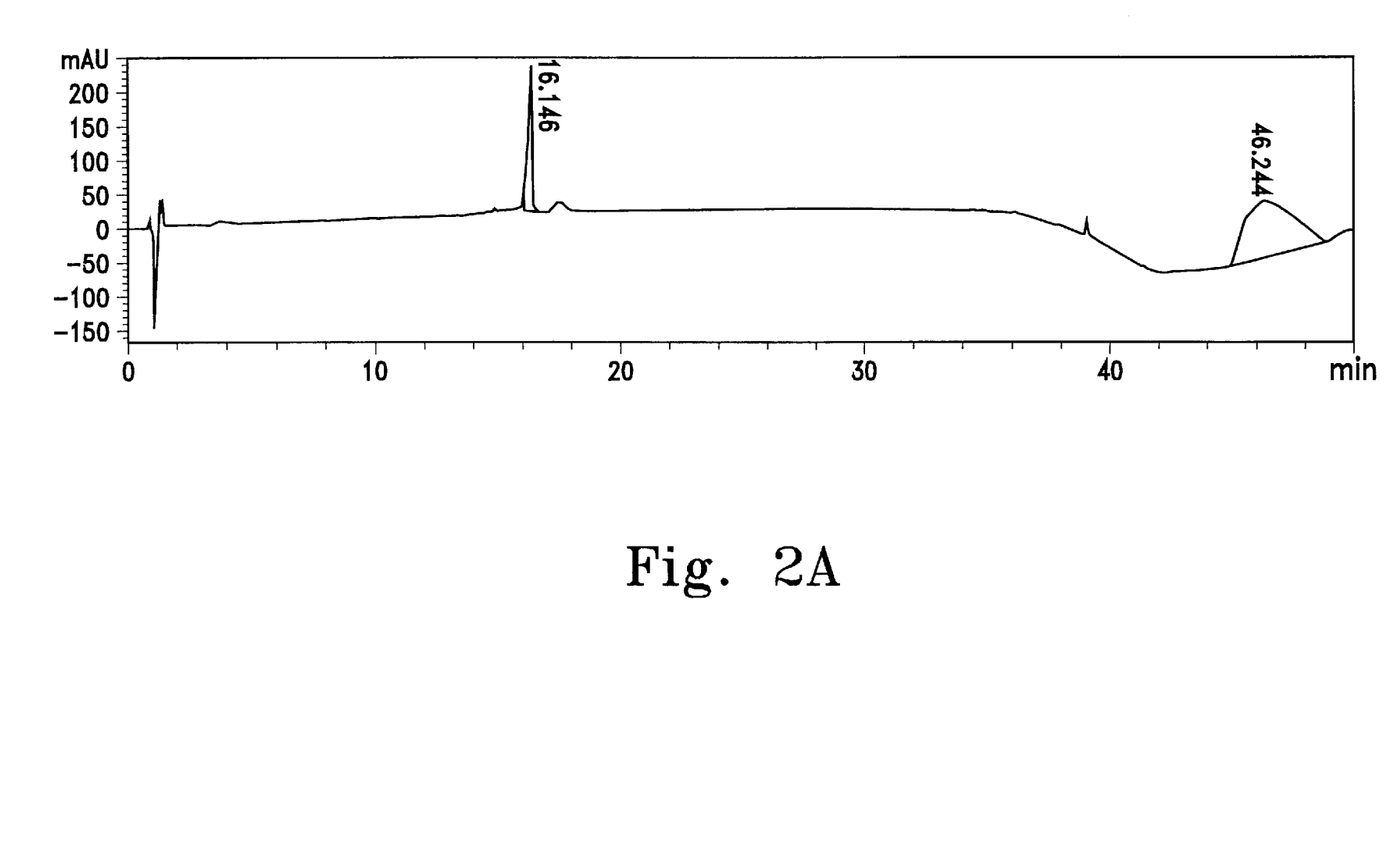
FIG. 2A is the HPLC chromatogram of the active fraction 7 (50% acetonitrile/water with 0.01% TFA). DAD1A; Sig= 210.4; Ref.=450.80; (E:\Jo52199\48000001.D). Peak at 16.146.
Figure 2B:
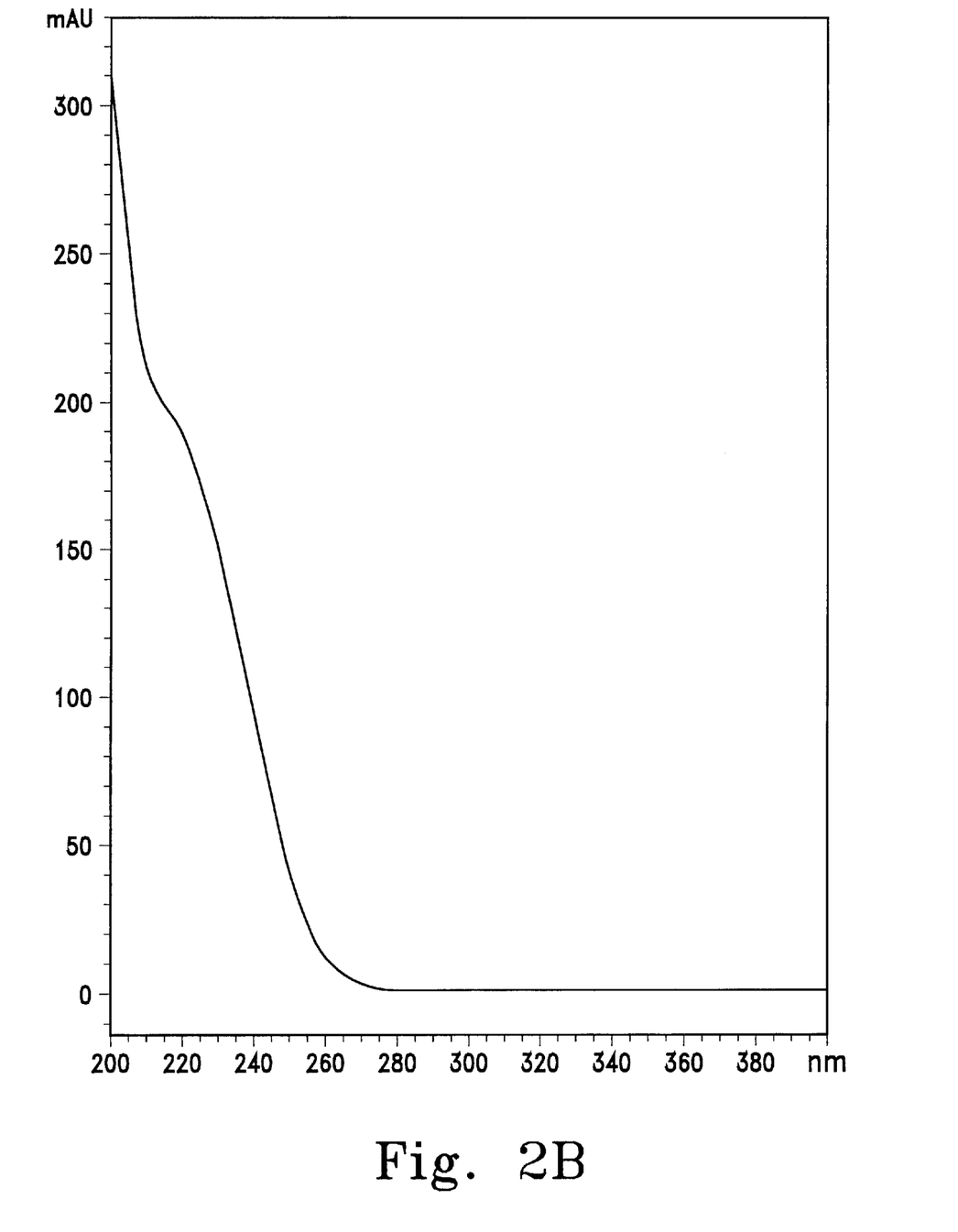
FIG. 2B is the UV apex spectrum of peak 16.146 (FIG. 2A) of 48000001.D. DAD1; 16.149 (314 mAU, Apx); Ref.=15.215 & 16.802 of 48000001.D.

The HPLC chromatogram of the active 50% acetonitrile/water with 0.01% TFA fraction and the HPLC chromatograms of the active fractions 6 and 7, including UV spectra of the active principles, are shown in FIGS. 1 and 2.

NRRL No. B-30145 most closely matched *Streptomyces mashuensis* by 16S RNA sequencing. Unlike the antibacterial metabolites typically associated with *S. mashuensis*, the fungicidal activity of NRRL No. B-30145 was extractable with butanol. *S. mashuensis* is known to produce streptomycin, which is a water-soluble antibacterial compound. Another antibiotic produced by *S. mashuensis*, monazomycin (Akasaki et al. 1963), does not display a shoulder at 215–220 nm as does the fungicidal active fractions of NRRL No. B-30145.

Antifungal compounds have also been found in the closely related and possibly synonymous species *Streptomyces griseocarneum* (American Type Culture Collection). These include porfiromycin (Claridge et al., 1986), a purple compound whose corresponding UV spectrum is not seen in the active fraction of NRRL No. B-30145 and the *Heptaenes trichomycin* (Komori and Morimoto, 1989) and griseocarnin (Campos et al., 1974), whose corresponding UV spectra are also not present in the active fraction. The fungicidal active is also not neutramycin, which is extractable with ethyl acetate (Mitscher and Kunstmann, 1969).

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

REFERENCES

Akasaki et al., "Monazomycin, a new antibiotic produced by a streptomyces," J. Antibiotics, vol. 16, pp 127–131 (1963).

Axelrood et al., "Douglas-fir root-associated microorganism with inhibitory activity towards fungal plant pathogens and human bacterial pathogens," Can. J. Microbiol., vol. 42, pp. 690–700 (1996).

Campos et al., "[Griseocarnin, an antifungal antibiotic isolated from *Streptoverticillium griseocarneum* (IA-7527)]," Rev Inst Antibiot (Recife), vol. 14(1–2), pp. 91–100 (1974) (English Summary only).

Chamberlain and Crawford, "In vitro and in vivo antagonism of pathogenic turfgrass fungi by *Streptomyces hygroscopicus* strains YCED9 and WYE53," J of Industrial Microbiol Biotechnol, vol. 23, pp. 641–646 (1999).

Claridge et al., "New mitomycin analogs produced by directed biosynthesis," J. Antibiotics vol. 39, pp. 437–446.

Crawford, "Use of Streptomyces bacteria to control plant pathogens," U.S. Pat. No. 5,527,526.

Komori and Morimoto, "Isolation of the aromatic heptaenic antibiotics trichomycin A-F by high-performance liquid chromatography," J. Chromatogr, vol. 481, pp 416 (1989).

Lechevalier, H. A., and S. A. Waksman, "The actinomycetes. III Antibiotics of actinomycetes", The Williams & Wilkins Co., Baltimore, p430ff, (1962).

Lechevalier, M. P, "Actinomycetes in agriculture and forestry," In M. Goodfellow, S. T. Williams, and M. Mordarski (ed.), Actinomycetes in biotechnology. Academic Press, Inc., New York, p. 327–358 (1988).

Mitscher, L. A. and M. P. Kunstmann, "The structure of neutramycin," Experientia vol. 25, pp. 12–3 (1969).

Reddi, G. S., and A. S. Rao, "Antagonism of soil actinomycetes to some soil-borne plant pathogenic fungi," Indian Phytopathol. Vol. 24, pp. 649–657 (1971).

Rothrock, C. S., and D. Gottlieb, "Role of antibiosis in antagonism of *Streptomyces hygroscopicus* var. *geldanus* to *Rhizoctonia solani* in soil," Can. J. Microbiol., vol. 30, pp. 1440–1447, (1984).

Schwinn et al., "Advances In Plant Pathology: *Phytophthora infestans*, The Cause Of Late Blight Of Potato," (Academic Press, San Diego, p. 244 (1991). Suh, "Antifungal biocontrol agents, a process for preparing and treating the same," International Patent Publication Number WO 98/35017.

Yuan and Crawford, "Characterization of *Streptomyces lydicus* WYEC108 as a potential biocontrol agent against fungal root and seed rots," Appl. Env. Microbiol. vol. 61, pp. 3119–28 (1995).

What is claimed is:

1. An isolated, biologically pure culture of Streptomyces sp. strain NRRL No. B-30145 and mutants thereof having all of the identifying characteristics of said strain NRRL No. B-30145.

2. A supernatant isolated from the culture of claim 1, wherein said supernatant does not exhibit activity against Rhizoctonia in agar diffusion assays.

3. A composition comprising the culture of claim 1, and a carrier.

4. The composition of claim 3, further comprising at least one chemical or biological pesticide, which in combination with said composition effectively treats fungal infections.

5. The composition of claim 3, wherein the composition is formulated from the group consisting of a wettable powder, a granule, an aqueous suspension, and emulsifiable concentrate and a microencapsulated formulation.

6. A butanol soluble metabolite produced by the Streptomyces sp. strain of claim 1 that exhibits activity against plant pathogenic fungi.

7. The metabolite of claim 6, wherein the metabolite is heat and base stable, is acid labile and has a molecular weight of less than 10,000 daltons.

8. A composition comprising the metabolite of claim 6 and a carrier.

9. The composition of claim 8, further comprising at least one chemical or biological pesticide, which in combination with said composition effectively treats fungal infections.

10. The composition of claim 8, wherein the composition is formulated from the group consisting of a wettable powder, a granule, an aqueous suspension, and emulsifiable concentrate and a microencapsulated formulation.

11. A method for protecting or treating plants, fruit, and roots from fungal infections comprising applying a fungicidal effective amount of the Steptomyces sp. strain of claim 1 to the plant, fruit, or root.

12. The method of claim 11, wherein the infections are caused by a fungus selected from the group consisting of *Alternaria solani, Botrytis cinerea*, Rhizoctonia sp., Sclerotinia sp., and Phytophthora sp.

13. The method of claim 11, wherein the Streptomyces sp. strain NRRL No. B-30145 is applied as a whole broth culture.

14. The method of claim 11, wherein the Streptomyces sp. strain NRRL No. B-30145 is applied as a supernatant.

15. The method of claim 11, wherein the Streptomyces sp. strain NRRL No. B-30145 is applied as a formulation selected from the group consisting of wettable powders, granules, aqueous suspensions, emulsifiable concentrates or microencapsulations.

16. The method of claim 13, further comprising applying an effective amount of at least one chemical or biological pesticide, which in combination with said strain effectively treats fungal infections.

17. A method for protecting or treating plants, fruit, and roots from fungal infections comprising applying a fungicidal effective amount of the metabolite of claim 6 to the plant, fruit or root.

18. The method of claim 17, wherein the infections are caused by a fungus selected from the group consisting of *Alternaria solani, Botrytis cinerea*, Rhizoctonia sp., Sclerotinia sp., and Phytophthora sp.

19. The method of claim 17, wherein the metabolite is applied as a whole broth culture.

20. The method of claim 17, wherein the metabolite is applied as a supernatant.

21. The method of claim 17, wherein the metabolite is applied as a formulation selected from the group consisting of wettable powders, granules, aqueous suspensions, emulsifiable concentrates or microencapsulations.

22. The method of claim 18, further comprising applying an effective amount of a least one chemical or biological pesticide, which in combination with said metabolite effectively treats fungal infections.

* * * * *